(12) United States Patent
Hoth et al.

(10) Patent No.: US 7,065,813 B2
(45) Date of Patent: Jun. 27, 2006

(54) PATIENT EXAMINATION SUPPORT SYSTEM

(75) Inventors: Tobias Hoth, Pegnitz (DE); Jürgen Plannerer, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 65 days.

(21) Appl. No.: 10/859,387

(22) Filed: Jun. 2, 2004

(65) Prior Publication Data

US 2004/0261177 A1 Dec. 30, 2004

(30) Foreign Application Priority Data

Jun. 4, 2003 (DE) ................................ 103 25 302

(51) Int. Cl.
*A61B 6/00* (2006.01)

(52) U.S. Cl. ................. 5/601; 5/943; 378/209

(58) Field of Classification Search .............. 5/601, 5/600, 611, 943, 610; 378/209
See application file for complete search history.

(56) References Cited

U.S. PATENT DOCUMENTS

| | | | | |
|---|---|---|---|---|
| 3,640,520 A | * | 2/1972 | Wieland et al. ............... 5/610 |
| 4,059,255 A | * | 11/1977 | Perold .......................... 5/610 |
| 4,131,802 A | * | 12/1978 | Braden et al. ................. 378/20 |
| 4,545,571 A | | 10/1985 | Chambron ..................... 5/601 |
| 4,568,071 A | * | 2/1986 | Rice ............................. 5/601 |
| 4,613,122 A | * | 9/1986 | Manabe ........................ 5/601 |
| 5,590,429 A | * | 1/1997 | Boomgaarden et al. ........ 5/600 |
| 6,459,923 B1 | * | 10/2002 | Plewes et al. ............... 600/411 |
| 6,484,332 B1 | * | 11/2002 | Korver et al. ............. 5/81.1 R |
| 2002/0104163 A1 | | 8/2002 | Reimann ...................... 5/601 |
| 2004/0261176 A1 | * | 12/2004 | Plannerer ...................... 5/601 |
| 2004/0261177 A1 | * | 12/2004 | Hoth et al. .................... 5/601 |

FOREIGN PATENT DOCUMENTS

| | | |
|---|---|---|
| DE | 27 43 427 | 5/1979 |
| DE | 101 03 331 | 8/2002 |

* cited by examiner

*Primary Examiner*—Robert G. Santos
(74) *Attorney, Agent, or Firm*—Brinks Hofer Gilson & Lione

(57) ABSTRACT

A patient examination support system comprises a support structure and a tabletop. The tabletop supported on the support structure is displaceable toward an examination region. The examination region is spaced apart from the support structure in a longitudinal direction of the tabletop, and a supporting arm, which is extendable from the support structure in a direction of the examination region, braces the tabletop.

22 Claims, 2 Drawing Sheets

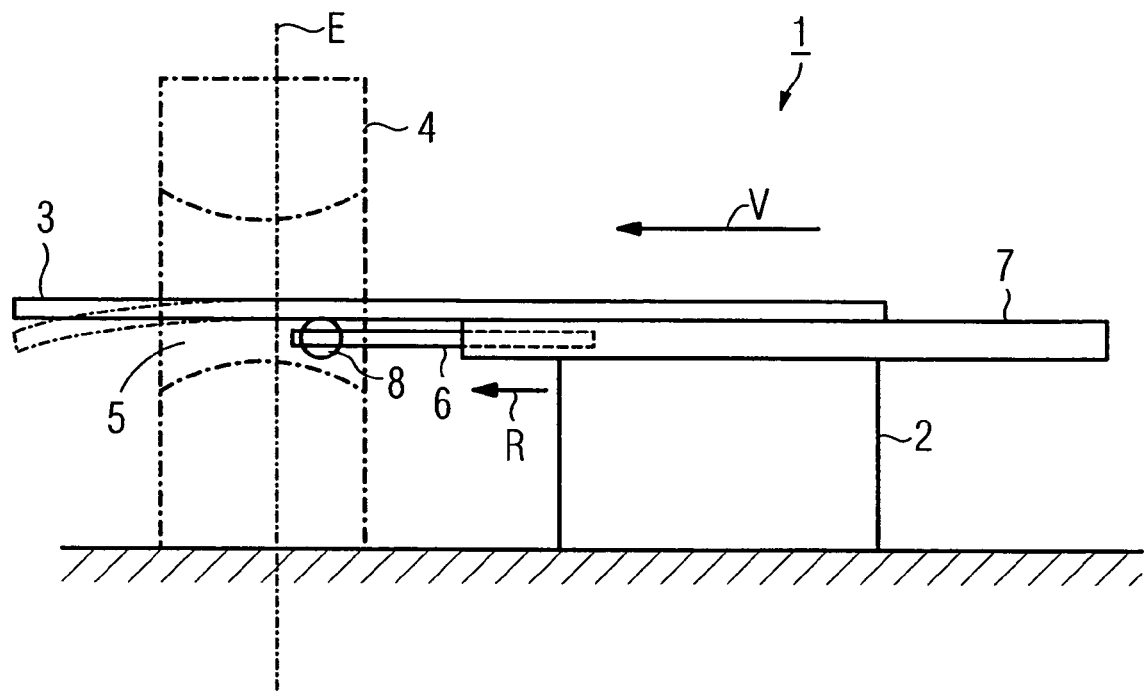
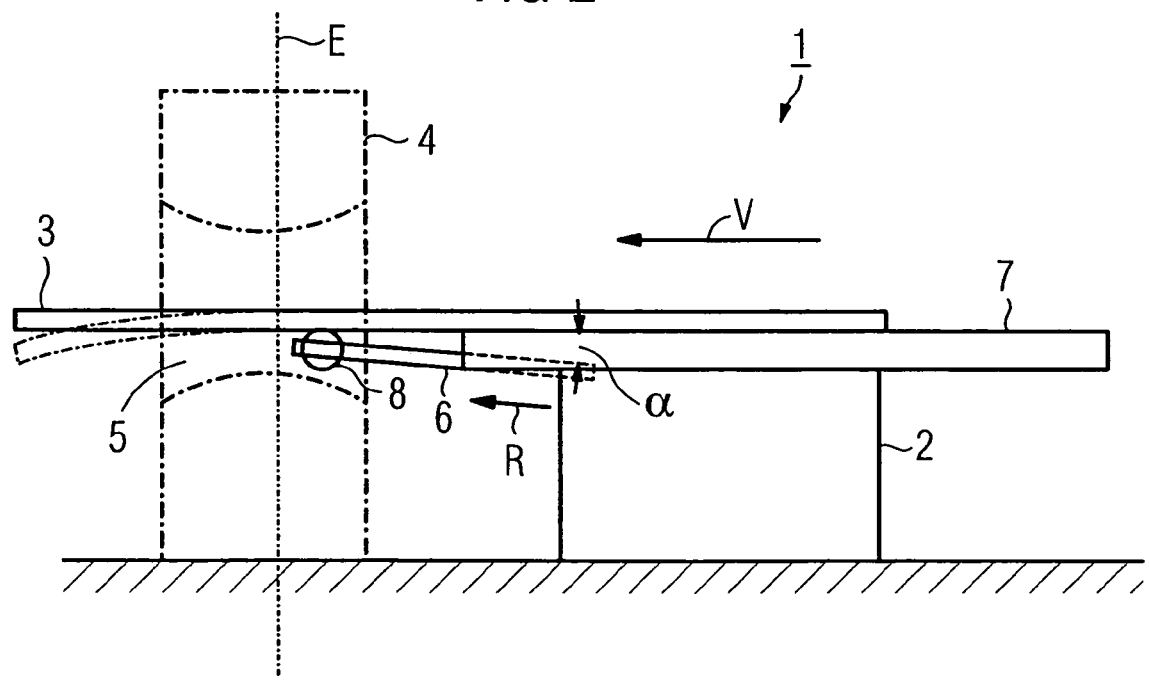

PATIENT EXAMINATION SUPPORT SYSTEM

BACKGROUND

The invention relates, in general, to clinical patient tables or support systems, and more particularly to a patient examination support system having a longitudinally displaceable tabletop which is supported on a support structure, with an examination region spaced apart longitudinally of the tabletop from the support structure.

A patient examination support system of this kind, particularly for a magnetic resonance imaging system or a computed tomography system, is known for instance from German Patent Disclosure DE 101 03 331 A1.

The patient examination support system known from DE 101 03 331 A1 is intended for an imaging medical examination system, in which a tabletop intended for supporting the patient is braced both on a supporting lifting structure and on an additional support pillar. The examination region in which a scanning process takes place is located between these supporting devices, in an unsupported region of the tabletop. However, bracing the tabletop in two places may not prevent sagging of the tabletop during an advancement motion while the tabletop has not yet reached the additional support pillar on a side opposite the lifting structure of the examination system.

SUMMARY

The present invention is defined by the appended claims. This description summarizes some aspects of the present embodiments and should not be used to limit the claims.

An object is to disclose a patient examination support system, in particular for a computed tomography system, with substantially little sagging of a tabletop, and in which an examination or treatment region for examining or treating a patient is spaced apart longitudinally of the tabletop from a support structure which carries the longitudinally displaceably supported tabletop. Other objects with or without the object described above may be provided by the embodiments herein.

A support structure provided to receive a tabletop has a supporting arm that braces the tabletop and that can be extended in a direction of an examination region. The supporting arm can be shifted, and in particular displaced, to near or into the examination region, and may have at least one bearing point for bracing the tabletop. In order to increase a range of adjustment of the tabletop, there may not be a need for a displaceable two-dimensional or frame-like intermediate part or a displaceable superstructure, which carries a load, including a load of the patient, as part of the support structure, embodied in particular as a lifting structure. The patient examination support system is thus constructed relatively simply, yet excessive sagging of the table is nevertheless minimized.

In comparison with a lifting and advancement apparatus with a parallelogram kinematical mechanism, for instance, it may also be advantageous that a horizontal positioning motion of the tabletop is substantially independent of the bracing action. As such, an adjusting device can be realized relatively simply in terms of drive and control technology and a precision of positioning may be dependent only on a drive mechanism and a closed-loop control circuit of the tabletop. It may also be advantageous that a compact clinical system formed with the supporting arm can be moved closer to components of a diagnostic system, in particular to a gantry of a computed tomography system, than can for instance be a displaceable superstructure of a patient examination tabletop. As a result, sagging of the table may be reduced still further.

In a preferred embodiment, an extension direction of the supporting arm may be oblique relative to the tabletop. Thus increasing a supporting force of the supporting arm exerted on the tabletop can be attained in a relatively simple way, the farther the supporting arm has been extended linearly out of the support structure. Thus, at least slight rising of the tabletop in the region that protrudes past the support structure via the supporting arm can be provided; this raising may be compensated for by the weight load exerted by the patient.

A slight relative mobility between the supporting arm and the tabletop is preferably assured by providing that on the supporting arm, at least in its front region, that is, the region spaced farthest apart from the support unit, at least one roller is supported, over which the tabletop can roll. The at least one roller may be wheel, a caster, a ball, or a cylinder. Alternatively, a sliding bearing between the supporting arm and the tabletop can be provided.

The support unit for the longitudinally displaceable support of the tabletop is preferably vertically adjustable. The supporting arm is preferably pivotably connected to an adjustable-height portion of the support structure, or patient supporting system; that is, when the patient support is being vertically adjusted, no vertical relative motion may occur between the supporting arm and the tabletop. The horizontal displacement of the tabletop in its longitudinal direction can be either decoupled from or synchronized with an actuation of the supporting arm. If these two motions are decoupled, then extending the supporting arm can be dispensed with, particularly when a patient or a specimen that does not weigh very much is being examined. Conversely, synchronization between the displacement of the tabletop and the extension of the supporting arm can be attained mechanically in a relatively simple way, for instance, by causing the tabletop, in a displacement, to carry the supporting arm along up to an optionally adjustable stop. An adjustment of the optionally adjustable stop is preferably contemplated as a function of the weight of the patient or specimen to be examined.

In another preferred embodiment, in addition to the support unit preferably embodied as a lifting structure, the patient examination support system has a further support pillar, on a side of the examination region remote from the support structure. Such an additional support pillar, preferably in a vertically adjustable embodiment, is known in principle from DE 101 03 331 A1. In that case, the support pillar is vertically adjustable either independently of the support structure or synchronously with the support structure.

The patient examination support system with the support pillar, in a first method of operation, is operated such that with the support pillar located in a low position, the tabletop is moved through the examination region, for instance through an opening in a computed tomography system, and the support pillar is extended upward until the tabletop is substantially horizontal. Once the horizontal position of the tabletop is reached, the support pillar and the examination structure, if necessary, may be extended upward synchronously until the patient, or the object to be examined, is positioned at a defined and desirable examination height. Alternately, if needed, the support unit can also be adjusted in a synchronized way with the support pillar, such that an arbitrary defined, even non-horizontal, position of the table is established.

In an alternatively preferred method of operation, the tabletop may first be likewise advanced through the examination region. Once the tabletop is located in the region of the support pillar, however, the support pillar is raised only far enough that it just touches the tabletop. Upon further advancement of the tabletop, the support pillar remains in the above discussed position, thereby preventing further sagging of the tabletop. Consequently, this method may prevent the patient from being raised again once the tabletop has reached the support pillar. The examination or treatment is thus performed with a defined, constant sagging of the tabletop.

Preferably, the support pillar, which can be vertically adjusted by a motor, is embodied with a position detection sensor and/or with a sensor which may indicate that the tabletop is resting on the support pillar. As a result—in cooperation with a measuring instrument in the support structure—or via a contact-less measuring instrument, the inclination or sagging of the tabletop is measurable.

One advantageous feature may reside in the fact that because any sagging of a longitudinally adjustable tabletop of an examination and/or treatment system is substantially minimized, examination and/or treatment parameters that may depend on the positioning of the tabletop are kept constant, virtually independently of the weight of the patient or specimen, during an entire advancement motion of the tabletop.

Illustrative and exemplary embodiments of the invention are described in further detail below with reference to and in conjunction with the figures.

BRIEF DESCRIPTION OF THE DRAWINGS

FIG. 1 is a schematic illustrating an embodiment of a patient examination support system;

FIG. 2 is a schematic illustrating another embodiment of a patient examination support system;

Elements or parameters corresponding to one another are identified by the same reference numerals in all the drawings.

DETAILED DESCRIPTION

Figure 3:
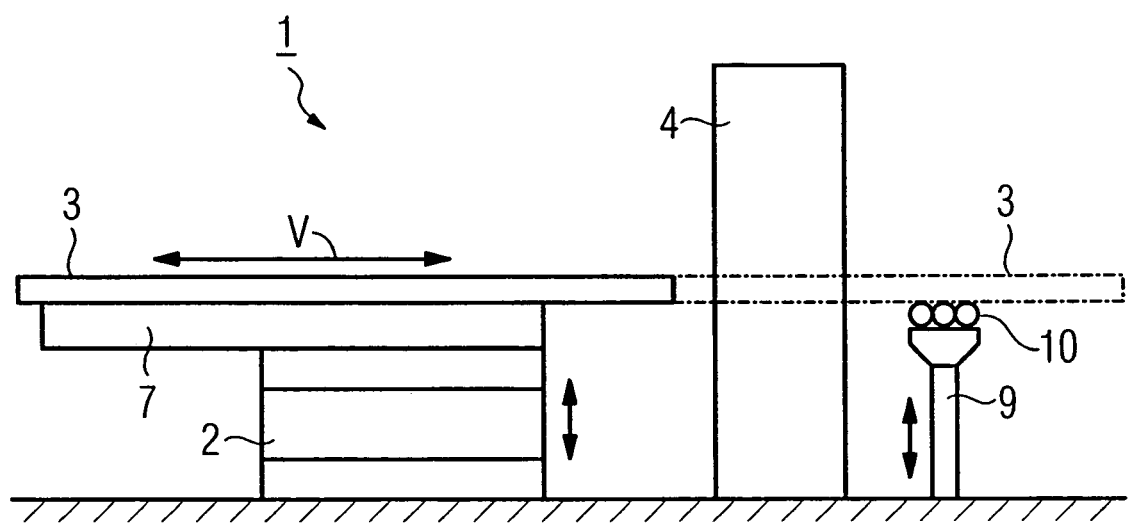
FIG. 3 is a schematic illustrating another embodiment of a patient examination support system with an additional support pillar.

The above, as well as other, advantages will become readily apparent to those skilled in the art from the following detailed description of preferred embodiments when considered in the light of the accompanying drawings.

FIGS. 1 and 2 are schematic views showing a patient examination support system 1. The patient examination support system 1 includes a support structure 2 embodied as a lifting structure, which supports a longitudinally displaceable patient examination tabletop 3. Spaced apart from the support structure 2 in the displacement direction V is a supporting arm clinical device or system 4, shown drawn in dashed lines, for instance a computed tomography system, which may predetermine an examination region 5 with a scanning plane E. No materials that may influence the examination of the patient should be present in the examination region 5, so that there can be no question of reinforcing the tabletop 3, for instance with metal reinforcing elements. Advantageously, the tabletop 3 is formed of radio-transparent material, such as fiber-reinforced plastic or hard polyurethane foam. The weight load exerted on the tabletop 3 by the patient may cause sagging, represented in the drawings with dashed lines to the left of the examination region 5. While the sagging outside the examination region 5 may not be relevant, such sagging should be minimized as much as possible in the scanning plane E. As such, a supporting arm 6 is provided, which is extensible out of a supporting platform 7, which as part of the support structure 2 may be vertically adjustable and may serve a purpose of displaceably supporting the tabletop 3. At least one roller 8 for bracing the table is supported on the end of the supporting arm 6 remote from the support structure 2. The supporting arm 6 including the at least one roller 8, as well as other parts, especially connecting parts, to the extent that a given part is capable of entering the examination region 5 and in particular the scanning plane E, are like the tabletop 3 made of materials that may affect the examination only insignificantly, if at all.

In the embodiment of FIG. 1, the supporting arm 6 is displaceable parallel to the tabletop 3 in the extension direction R. In this case, upon displacement of the tabletop 3 through the scanning plane E, provision is made so that the supporting arm 6 will be carried along with the tabletop 3 as far as a fixedly defined stop.

In the embodiment of FIG. 2, the extension direction R of the supporting arm 6 may form an acute angle $\alpha$ with the tabletop 3 with the acute angle remaining constant as the tabletop is displaced from the support structure. As a result, the farther the supporting arm 6 has been extended out of the support structure 2, the farther the roller 8 may be lifted. Because of the small size of the angle $\alpha$, which may be less than 10° and in particular less than 5° and for instance approximately 3°, a relatively great adjustment of the supporting arm 6 in the extension direction R may correspond to only a relatively slight vertical adjustment of the roller 8 perpendicular to the displacement direction V. Thus, despite the fact that adjusting the supporting arm 6 involves relatively great tolerances, a very precise vertical adjustment of the roller 8 is possible.

The supporting arm 6 can be set such that in an unloaded state, the roller 8 would protrude slightly past a lower edge of the tabletop 3, that is, the lower edge that is to be braced, and be brought into the intended position, which is the position shown in FIG. 2, by the weight load exerted by the patient or by the specimen to be examined on the table. An elastic deformation of the supporting arm 6 is thus exploited all the more, the greater the weight of the patient or specimen that loads the tabletop 3 in the examination region 5. The supporting arm 6 can be extended to close to the scanning plane E but may not intersect it.

Figure 4:
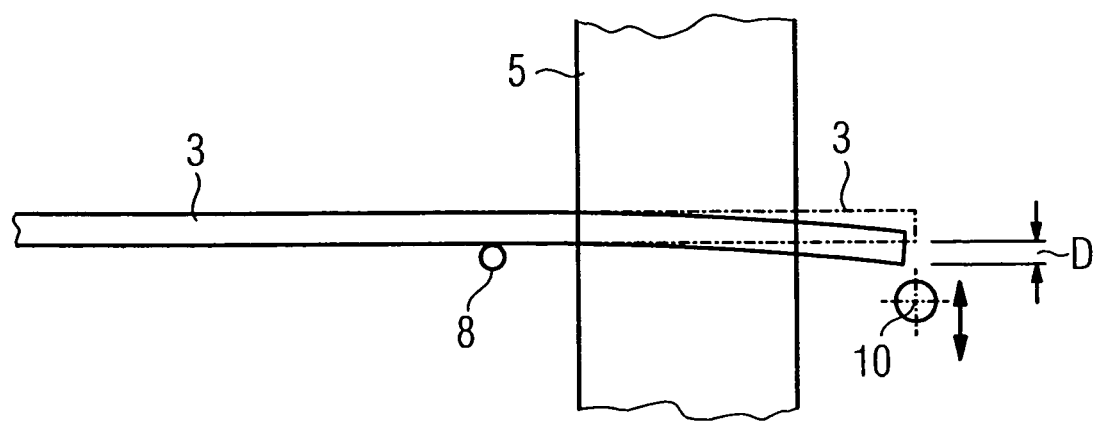
FIG. 4 is a fragmentary view of the patient examination support system of FIG. 3, with a partly sagging tabletop.

The embodiment of FIGS. 3 and 4 has a patient examination support system 1 with an additional support pillar 9, which like the support structure 2 is vertically adjustable, but which may be disposed on the opposite side of the examination region 5. A supporting arm 6 for the support structure 2 is not shown in FIG. 3, while in FIG. 4 the roller 8 of the supporting arm 6 is visible. Alternatively, the roller 8 can be secured to a superstructure of the patient examination support system 1. The exemplary embodiment shown can also be adapted to other embodiments without the supporting arm 6 that is extendible out of the support structure 2.

The support pillar 9, that may be vertically adjustable by a motor, may have a plurality of rollers 10, which analogously to the roller 8 of the supporting arm 6, may serve to provide easier displaceability or adjustment of the tabletop 3 in the displacement or advancement direction V. Alternatively or in addition, a sliding guidance of the tabletop 3 can be provided in this case as well. In a first alternative method, once the tabletop 3 reaches the support pillar 9, which at first has been lowered somewhat, the support pillar 9 is raised enough that the tabletop 3 upon further advancement is kept substantially horizontal, practically without any substantial sagging. In a second, especially preferred alternative method, the support pillar 9 moves just up to the tabletop 3 and may prevent additional sagging in the course of the further advancement of the tabletop 3. As can be seen from FIG. 4, the support pillar 9, as soon as it has been brought to the somewhat sagging tabletop 3, remains, in the course of the further advancement of the table, at a height somewhat below the height of the roller 8. For performing this method, the patient examination table system 1 has measuring instruments and adjusting devices, not shown, such as at least one sensor for determining the sagging D and/or the angle α of the tabletop 3 with a horizontal line.

The support pillar 9 may be spaced far enough apart from the examination region 5 to enable a pivoting motion of the supporting arm clinical device 4 that might be necessary during the examination. The pivotability of the supporting arm clinical device 4 is likewise unimpaired by the supporting arm 6 that reaches partway into the examination region 5 (FIGS. 1 and 2).

If the supporting arm 6 permits the vertical adjustment of the roller 8, as described in conjunction with FIG. 2, then the method for vertical adjustment, using the measuring instruments and adjusting instruments not shown, can also include both the supporting arm 6 and the roller 8.

The invention claimed is:

1. A patient examination support system, comprising:
a support structure;
a tabletop, the tabletop being supported on the support structure and displaceable toward an examination region; and
a supporting arm, which is extendable from the support structure in a direction of the examination region, positioned to brace the tabletop,
wherein the examination region is spaced apart from the support structure in a longitudinal direction of the tabletop and the directional extension of the supporting arm forms an acute angle (α) with the tabletop, the acute angle (α) remains constant as the tabletop is displaced from the support structure.

2. The patient examination support system of claim 1, wherein the supporting arm has at least one roller at a remote position from the supporting structure, the at least one roller operable to directly support the tabletop at the remote position during the displacement of the tabletop from the support structure.

3. The patient examination support system of claim 1, wherein the supporting arm has at least one roller at a remote position from the supporting structure, the at least one roller is operable to protrude slightly past a lower edge of the tabletop in an unloaded state before the lower edge is braced by the at least one roller.

4. The patient examination support system of claim 1, wherein the support structure is vertically adjustable and operable to support primarily horizontal displacement of the tabletop from the support structure.

5. The patient examination support system of claim 1, wherein the extension of the supporting arm is synchronized with the primarily longitudinal displacement of the tabletop, the tabletop and supporting arm being movable with respect to each other.

6. The patient examination support system of claim 1, wherein the examination region is defined by a pivoting motion of an arm of a clinical system.

7. The patient examination support system of claim 1, further comprising a support pillar disposed on a side of the examination region remote from the support structure, the support pillar positionable for additional support of the tabletop.

8. The patent examination support system of claim 7, wherein the support pillar is vertically adjustable.

9. The patient examination support system of claim 7, wherein the support pillar has at least one roller over which the tabletop rolls.

10. The patient examination support system of claim 7, wherein the support pillar provides a sliding guidance to the tabletop.

11. The patent examination support system of claim 7, wherein a height of the support pillar is such that the tabletop is substantially horizontal.

12. The patient examination support system of claim 7, wherein a height of the support pillar that slidingly guides the tabletop in the displacement of the tabletop is set to a height below that of the supporting art.

13. The patient examination support system of claim 9, wherein a height of the at least one roller of the support pillar that guides the tabletop in the displacement of the tabletop is set to a height below that of the at least one roller of the supporting arm.

14. The patient examination support system of claim 7, wherein the support pillar is spaced away from the examination region to enable a pivoting motion of a clinical system during an examination of a patient, the pivoting motion of the clinical system is substantially unimpaired by the supporting arm that reaches partway into the examination region.

15. The patient examination support system of claim 1, further comprising an adjusting system provided to primarily horizontally position the tabletop and to control the supporting arm.

16. A patient examination support system, comprising:
a support structure;
a tabletop, the tabletop being supported on the support structure and displaceable toward an examination region, the examination region is spaced apart from the support structure in a longitudinal direction of the tabletop;
a supporting arm, which is extendable from the support structure in a direction of the examination region, positioned to brace the tabletop; and
an adjusting system provided to position the tabletop and to control the supporting arm,
wherein a substantially precise positioning of the tabletop is dependent on a drive mechanism and a closed-loop control circuit of the tabletop.

17. The patient examination support system of claim 16, wherein the directional extension of the supporting arm forms an acute angle (α) with the tabletop.

18. A patient examination support system, comprising:
a support structure;
a tabletop, the tabletop being supported on the support structure and displaceable toward an examination region, the examination region is spaced apart from the support structure in a longitudinal direction of the tabletop;

a supporting arm, which is extendable from the support structure in a direction of the examination region, positioned to brace the tabletop; and an adjusting system provided to position the tabletop and to control the supporting arm, wherein a substantially precise control of the supporting arm is dependent on a drive mechanism and a closed-loop control circuit of the supporting arm.

19. The patient examination support system of claim 18, wherein the directional extension of the supporting arm forms an acute angle ($\alpha$) with the tabletop.

20. A patient examination support system, comprising:

a support structure;

a tabletop, the tabletop being supported on the support structure and displaceable toward an examination region; and a supporting arm, which is extendable from the support structure in a direction of the examination region, the supporting arm having at least one roller at a remote position from the supporting structure, the at least one roller operable to directly support the tabletop at the remote position during the displacement of the tabletop from the support structure, wherein the examination region is spaced apart from the support structure in a longitudinal direction of the tabletop.

21. The patient examination support system of claim 20, wherein the directional extension of the supporting arm forms an acute angle ($\alpha$) with the tabletop, the acute angle ($\alpha$) remains constant as the tabletop is displaced from the support structure.

22. The patient examination support system of claim 20, wherein the tabletop is manufactured from radio-transparent material.

* * * * *